United States Patent [19]

Vance et al.

[11] Patent Number: 5,358,472
[45] Date of Patent: Oct. 25, 1994

[54] GUIDEWIRE ATHERECTOMY CATHETER AND METHOD OF USING THE SAME

[75] Inventors: Jeffrey D. Vance, Hugo; Rick L. Shockey, Coon Rapids, both of Minn.

[73] Assignee: Schneider (USA) Inc., Plymouth, Minn.

[21] Appl. No.: 118,949

[22] Filed: Sep. 9, 1993

Related U.S. Application Data

[63] Continuation of Ser. No. 819,853, Jan. 13, 1992, abandoned.

[51] Int. Cl.⁵ .............................................. A61B 17/22
[52] U.S. Cl. ........................................ 604/22; 606/159
[58] Field of Search ....................... 606/159, 170, 180; 604/22

[56] References Cited

U.S. PATENT DOCUMENTS

| | | |
|---|---|---|
| 4,207,874 | 6/1980 | Choy . |
| 4,748,979 | 6/1988 | Hershenson . |
| 4,762,120 | 8/1988 | Bonzel . |
| 4,784,636 | 11/1988 | Rydell . |
| 4,857,045 | 8/1989 | Rydell . |
| 4,895,166 | 1/1990 | Farr et al. . |
| 4,950,238 | 8/1990 | Sullivan . |
| 4,950,277 | 8/1990 | Farr ...................... 606/159 |
| 5,084,010 | 1/1992 | Plaia et al. ............... 604/22 |

Primary Examiner—Michael H. Thaler
Attorney, Agent, or Firm—Haugen and Nikolai

[57] ABSTRACT

An atherectomy catheter device includes an improved guidewire system including a guidewire port member secured to the distal tip portion of the outer tubular member of an atherectomy catheter of the coaxial type having large and small concentrically disposed elongated flexible tubular members with a rotating cutter member fixed to the distal end of the inner tubular member. The guidewire is spaced from the cutter head yet controls the cutter disposition relative to the vessel lumen of interest. The inner and outer tubular members are constructed to simultaneously provide flushing liquid and aspirate the cutting site. A method of using the improved catheter is also disclosed.

8 Claims, 2 Drawing Sheets

GUIDEWIRE ATHERECTOMY CATHETER AND METHOD OF USING THE SAME

This is a continuation of copending application Ser. No. 07/819,853, filed on Jan. 13, 1992 now abandoned.

BACKGROUND OF THE INVENTION

I. Field of the Invention

The present invention generally pertains to a relatively non-invasive plaque resolving device of the class adapted to be inserted through the lumen of a blood vessel and manipulated therethrough to a desired location to ply a cutting tool to excise deposits of atherosclerotic plaque from the internal surfaces of the vessel. More particularly, the present invention relates to a guidewire for use in conjunction with such a system.

II. Related Art

Impairment of the circulation of blood occasioned by intraarterial deposits of atherosclerotic plaque is a major symptom of cardiovascular disease. Obstruction of coronary arteries can lead to tissue death because of oxygen deprivation of heart muscle. Coronary infarction (heart attack) is the result. Plaque-induced stenosis of other major arteries can result in impairment of peripheral organ function. One long-used procedure for overcoming such obstructions and blockages involves a surgical by-pass operation in which the obstructed arteries are subtended by patient autographed blood vessels removed from other parts of the patient's body. Surgically invasive endarterectomy has also been used with limited success for clearing obstructed vessels.

The need has long existed for a less invasive and radical procedure to alleviate such blockages and achieve transmyocardial revascularization, or the like, in a manner which causes no significant damage to the healthy endothelial lining of the surrounding vessel. One technique that attempts to fulfill this need is balloon angioplasty in which an inflatable balloon is passed to the stenotic region of the affected artery and inflated with a fluid to a pressure (normally, about 5 atmospheres) to depress the plaque against the arterial wall thereby opening up the arterial volume. Because circulation is grossly impaired, however, balloon inflation/deflation must occur in a matter of seconds to avoid infarction. In addition, limited force is available because of the fear of damage to the arteries caused by overpressurization of the balloon. Also, the capture of plaque debris that may slough during the expansion process is not as yet provided for by such devices.

Other approaches include the use of a laser to clear obstructions in vessels as proposed, for example, in U.S. Pat. No. 4,207,874 to Choy. In that device, laser energy is conveyed by flexible fiberoptics in conjunction with a venial catheter and applied to the plaque obstruction in the occluded zone. In conjunction with this system various axial channels may be provided with appropriate fluid management manifolds in order to inject saline, aspirate debris with the saline and inject die for visualization. Additional coherently aligned fibers may be provided for actual viewing of the obstruction intraluminally. In addition to Choy, many other approaches utilizing variations on a laser excising system have also been proposed. Lasers, for example, have been utilized to resolve plaque by heating a catheter tip in a manner which causes the plaque tissue to, in effect, be melted away by the heated tip of the catheter resulting in permanent removal. The approach is illustrated by Hershenson in U.S. Pat. No. 4,748,979. A variety of cutting devices have also been proposed in conjunction with a catheter in which rotating cutters actually address and excise the stenosis. Most of these devices, however, appear to be ineffective for rapid cutting of the stenosis without affecting or damaging the relatively soft adjacent wall of the arterial vessel involved. U.S. Pat. No. 4,784,636 to Rydell is assigned to the same assignee as the present invention and illustrates such a device, an atherectomy catheter which includes a self-guiding catheter having an inflatable balloon disposed on the distal end portion thereof, the guide catheter being dimensioned to receive in its lumen an elongated drive tube having a rotational drive mechanism at its proximal end for rotating an angular cutting tip affixed to the distal end. In use, the guide catheter with the drive tube and cutter head retracted is advanced up to the occlusion, the balloon is inflated to lock the distal end in place and the cutter is rotated at high speed and advanced into the occlusion, while blood and any loose particular matter is aspirated. The balloon is then deflated and advanced further into the lesion and the steps repeated until the occlusion is removed.

A more recently issued patent to Rydell, common of assignee with the above invention, is U.S. Pat. No. 4,857,045, also directed to a self-guiding atherectomy catheter system, utilizes a coaxial system of inner and outer flexible tubular members in which the inner tubular member is journaled for rotation at the distal end of the outer tubular member. A motor located at the proximal end of the catheter assembly drives the inner tubular member including a dome-shaped rotational cutting head containing a number of substantially round open ports for addressing blockage material upon rotation which is fixed to the inner tubular member just beyond the end portion of the outer tubular member. Aspiration is accomplished through the inner tubular member and a flushing fluid such as saline administered through the outer tubular member, as required.

While the last-discussed system represents an improvement with regard to centering and operating the atherectomy catheter within the vessel of interest, there remains a need to improve the efficacy of such devices with respect to complete stenosis removal. There also exists a need to improve the ability of the operator to guide the catheter in navigating the vascular system particularly with regard to precise positioning of the cutter at the situs of the occlusion of interest. Positioning the cutter with respect to the blockage about the periphery of the vessel is difficult to achieve without a controlling guidewire. Guidewires have been used with success in several types of over-the-wire catheter systems but heretofore they have not been used with rotating atherectomy devices because of the need to coordinate the guidewire placement to avoid the cutter head.

Of particular interest is the so-called Monorail ™ catheter which has been used in connection with angioplasty balloon catheters with great success. In that system only a small distal segment of the balloon catheter actually passes over the guidewire with the remaining portion of the guidewire then extending generally along the exterior wall external to the catheter in the proximal direction. The short segment at the distal end provides the necessary control. The Monorail ™ catheter and its use is more particularly described in the Bonzel U.S. Pat. No. 4,762,129.

With respect to the present invention, there remains a need to provide more precise positioning of an atherectomy catheter within the vessel of interest to assure proper and complete removal of the occlusion. This is true not only for navigating the catheter along the vessel but also for proper positioning of the cutter with respect to the material to be removed.

SUMMARY OF THE INVENTION

The present invention provides an atherectomy catheter device including an improved Monorail ™ type guidewire system capable of operating in combination with a high speed rotary cutting head. The system further has the ability to simultaneously infuse flushing solution to cleanse and aspirate the treatment area to remove the flushing solution and all the debris from the site during the atherectomy procedure.

The system includes a guidewire port secured to the distal tip portion of the outer tubular member of an atherectomy catheter of the coaxial type having large and small concentrically disposed elongated flexible tubular members. The rotating cutting member is fixed to the distal end of the inner tubular member. The cutting member itself is a substantially hollow cylindrically symmetrical body having a symmetric distal, preferably of an elliptical or ogive shape, nose portion containing a plurality of openings extending along and rearward from the nose. The openings are in communication with the hollow interior and radially disposed about the tip. Each opening has an edge which operates to excise tissue upon rotation of the cutting tool and the excised tissue is generally directed into the hollow interior of the cutting tool. Such a tool is more fully described in copending application Ser. No. 07/819,780, filed of even date and assigned to the same assignee as the present application. If additional details from that application be necessary to the completion of the description herein, such may be deemed incorporated herein by reference.

The coaxial elongated flexible tubular members have sufficient clearance between each other such that flushing liquid may be introduced into the lumen of the outer tubular member and passed out through one or more radial ports near the distal end of the outer tubular member. The inner tubular member is secured to a drive means at its proximal end which is configured to rotate the inner tubular member, and with it the cutting tool, at relatively high speed while allowing the simultaneous infusion of a liquid through the outer tubular member and the aspiration of fluids through the lumen of the interior tubular member.

The improved Monorail ™ guidewire system associated with the invention includes an elongated guidewire port fixed to the outside of and parallel to the outer tubular member of the coaxial atherectomy catheter. The distal end of the port is located adjacent the distal end of the outer tubular member. The port is of a length and inner diameter which can optimize the operation of the particular guidewire desired to be used with the system. A typical guidewire might have a nominal diameter in the range of 0.010–0.025 inches.

The guidewire of the present invention can provide assistance in navigating the coaxial catheter through the vascular system to reach the site of the blockage of interest or be installed through the guidewire port after the catheter is substantially at the site in a well-known manner.

The mounting of the guidewire port radially outward of the larger tubular member allows and aids in securing the guidewire near but without interfering with the independent rotational operation of the cutting tool. The guidewire is capable of precisely positioning and maneuvering the cutting head relative to the blockage material to be excised. In this manner, the cutting head may be turned about the guidewire as a central axis to accurately position the cutting tool throughout 360° of the vessel's circular periphery to improve control of the cutting of the stenosis.

Briefly, in operation, upon insertion, the catheter is advanced within the patient's vascular system using the guidewire until the distal tip portion thereof is at the site of the lesion to be excised. The guidewire is used to maneuver and positively place the cutter in the desired location. The site is flooded with a flushing liquid and the cutter is driven at high speed and advanced into the lesion. The flushing fluid and debris suctioned from the lesion are aspirated through the hollow cutting tool into the lumen of the inner tubular member and are collected in a suitable vessel at the proximal end of the assembly.

DETAILED DESCRIPTION

The present invention involves improved control for an atherectomy catheter of the class in which a rotatable cutting tool is disposed at the distal end and in which means are provided at the proximal end for driving the cutter at a high rotational speed. The invention provides an improved guidewire system to control and positively position the cutting tool within a vessel for excising stenosis throughout 360° of the inner periphery of the vessel of interest. The system also allows the simultaneous infusion of a flushing liquid to cleanse the treatment site and provide for the aspiration of the flushing liquid and debris at the treatment site.

Figure 1:
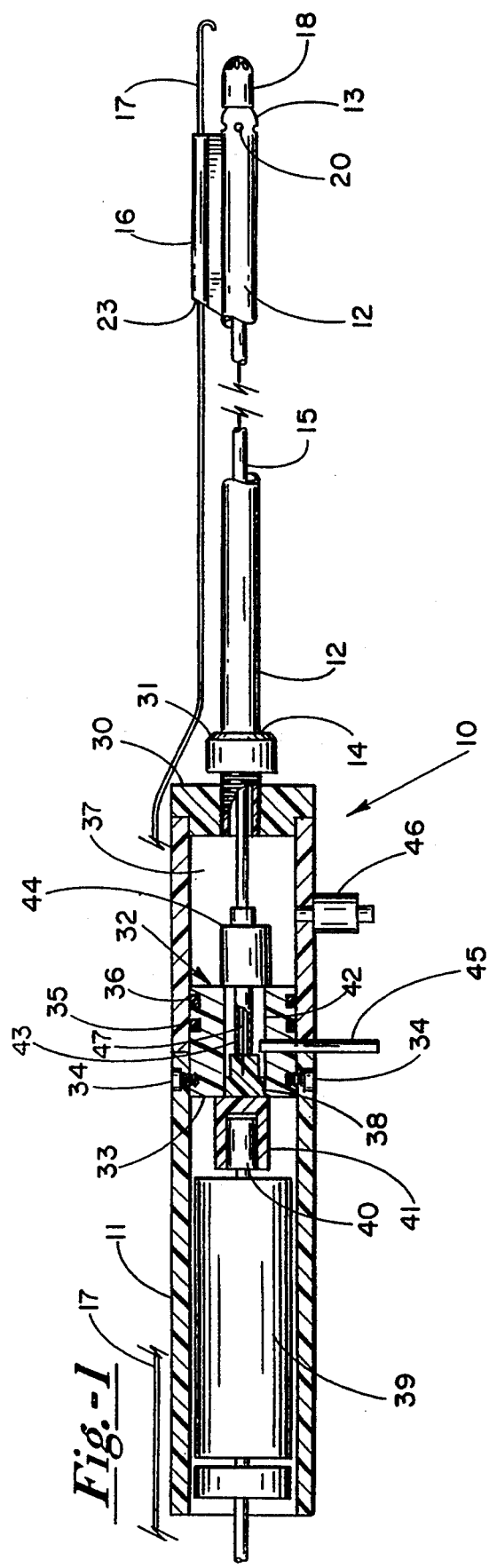
FIG. 1 is a view, partially in section, and with parts cut and broken away, illustrating an atherectomy catheter employing the guidewire system of the present invention.

The invention will next be described with particular reference to the drawing figures in which like numerals will be utilized to designate like parts throughout the same. FIG. 1 illustrates a surgical device including the guidewire and infusion/aspiration system of the present invention. The atherectomy catheter system is indicated generally by the numeral 10 and includes a proximal housing 11 containing the control and drive system, which may be of high impact plastic material. The catheter itself is of the concentric or coaxial type. The housing 11 is connected to an elongated outer flexible tubular member 12 extending between a distal end 13 and a proximal end 14 fixed to the housing 11. The hollow lumen of the outer tubular member 12 carries a coaxial elongated, flexible inner tubular member 15 which extends the full length of the outer tubular member 12. The outer tubular member 12, in the embodiment of FIG. 1, also carries a hollow stationary guidewire port 16 fixed to the outer surface of the outer tubular member 12 and which has a guidewire 17 threaded therethrough and which extends the full length of the system but independent of the catheter other than in conjunction with the guidewire port.

Figure 2:
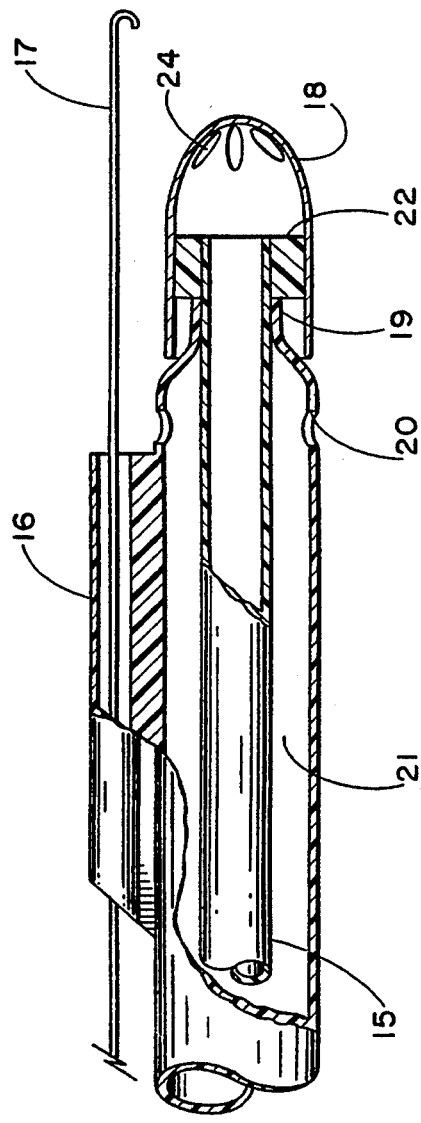
FIG. 2 is a greatly enlarged fragmentary view, with parts cut away, of one cutter head arrangement employing the guidewire system.

As can better be seen in FIGS. 2 and 3, and will be described in greater detail below, the distal end of the catheter carries a rotatable cutting head or cutting tool 18 which is fixed to and driven by the inner tube member 15 and is free to rotate about the outer tube member 12. The outer tube 12 is tapered or necked down to a distal end portion 19 creating a bearing surface which allows easy journaled rotation of the inner tube 15 and cutter head 17 during the excising procedure.

Figure 3:
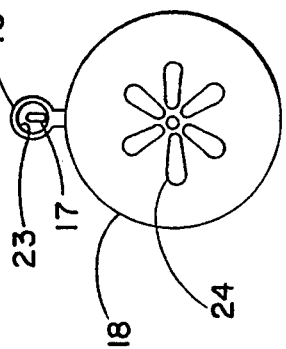
FIG. 3 is an end view of the cutter head and guidewire port of FIG. 2 still further enlarged.

An infusion system is provided including an indented annular area of reduced diameter near the distal end of the outer tubular member 12 which contains a series of radially disposed openings or holes 20 (FIG. 3). Liquid introduced into the annular space in the lumen of the member 12 surrounding the member 15 as at 21 can be ejected through the holes 20 to flush the operating site. An annular spacer member 22 is provided which is bonded both to the distal tip of the inner tubular member 15 and the inner surface of the cutting tool 18 to fix the cutter head to the distal tip of the inner tubular member 15.

The guidewire 17 extends through the central opening 23 in the guidewire port 16 and extends along the length of but outside of the catheter itself. It is further held at a distance from the cutting tool 18 so as not to interfere with the operation (rotation) of the cutting tool but is disposed to properly position and move the cutter head within the lumen of the vessel of interest as desired. The cutter head 18 contains a plurality of elongated openings 24 disposed in radial symmetry about the center of the distal nose as shown in FIG. 3. The preferred cutting tool is initially cylindrical and tapers off in an elliptical fashion as it approaches the distal end. The plurality of openings 24 is usually an even number from two to six and the openings are placed close to the nose of the elliptical cutting tool 18 so that the possibility of contacting and accidentally cutting the side wall of the vessel from which the plaque or other obstruction is to be excised is virtually eliminated.

A drive means is contained within the rigid tubular housing 11 located at the proximal end of the outer tubular member. The drive functions to rotate the inner tubular member within the lumen of the outer tubular member. The outer tubular member is joined to the tubular housing 11 as through end plug member 30 and is secured as by a compression fitting 31 which creates a liquid-tight seal. A rotary union shown generally at 32 is positioned within the housing 11 and includes a stationary tubular sleeve member 33 fixed to the housing 11 by pins or screws 34. A pair of O-ring seals 35 and 36 are disposed in annular grooves in the tubular sleeve 33 to preclude flushing liquid contained in the chamber 37 from passing beyond the rotary union.

The stationary sleeve 33 contains a rotating hollow manifold member 38 which rotates within the bore of the member 33 when driven by a motor such as that depicted generally at 39 having a drive shaft 40 and a coupling 41 connected in driving relation to the proximal end of the hollow manifold member 38. The hollow manifold member 38 further contains an annual recess 42 connected to a central bore 43 which, in turn, is joined to the proximal end of the inner elongated flexible tubular member 15 by a coupling member 44. The central inner bore 43, via the annular recess 42, is connected to a further tubular fitting 45 which passes through a bore in sleeve member 33 and the housing 11 to provide a suction outlet for the inner elongated flexible tubular member 15 via opening as at 47. Flushing saline or other solution input is provided through a further access tube 46 which extends through an additional bore in the housing 11 which communicates with the chamber 37.

In operation, the elongated catheter assembly is appropriately introduced into the vascular system as through the femoral artery, and, utilizing the guidewire 17, is advanced through the vascular system to the appropriate arterial or other location of interest placing the cutter tip 18 adjacent to the atheroma or other lesion or blockage material to be excised from the vessel. The cutting tool is precisely positioned and then operated at high speed to excise the lesion.

Figure 4:
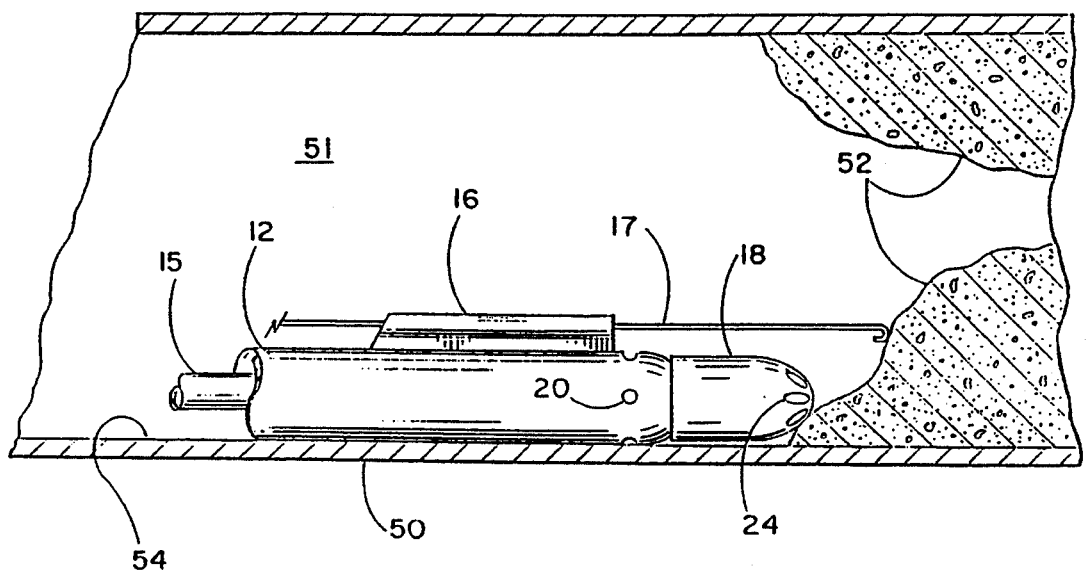
FIG. 4 is a view illustrating the embodiment of the cutter head of FIG. 2 in situ in a vessel.
Figure 5:
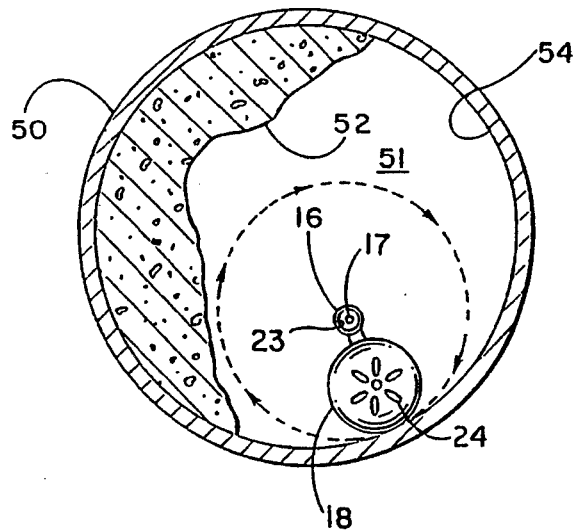
FIG. 5 is an end view of the embodiment of FIG. 4.

The large representations of FIGS. 4 and 5 shown partly as schematics illustrate a use of the device. In FIG. 4, an artery wall is shown in section at 50 which defines the hollow lumen or interior of the artery 51. A stenotic lesion is illustrated at 52 adhering to the inner surface of the arterial wall 50 and severely narrowing the cross sectional area of the passage through the lumen 51. FIG. 4 further illustrates the cutter tip 18 adjacent the lesion in a position to begin the excising operation. A specially designed guidewire 17 is utilized in conjunction with the guidewire port 16 which can be used to position the cutter head 18 with respect to the arterial wall 50 in a controlled manner.

As better illustrated in FIG. 5, the guidewire 17 can be used to rotate the cutter head 18 about the periphery of the inner surface of the wall of the vessel of interest to control the peripheral excising of the stenotic lesion 52. The guidewire is in a position to sense the presence or absence of blocking material and operates in a manner such that it easily clears the rotating cutting tool 18 which is free to rotate independent of the guidewire. The cutting tool 18 can then be precisely maneuvered until the entire stenotic lesion 32 is removed from the inner surface 54 of the arterial wall 50. It will further be appreciated that the guidewire 17 can be utilized to more precisely aim the tip of cutting member 18 with respect to the stenosis so that excision can take place right up to the wall but without damaging the inner lining of the arterial wall at 54.

During the time of excision, of course, the area is continually flushed with saline, or the like, introduced through the fitting 46 and flowing through the lumen of the outer tubular member 12 and outward through the radial ports 20. This keeps the excised debris in solution. A suitable source of suction is simultaneously applied to the fitting 45 which operates through the inner tubular member 15 to aspirate the site through the cutting tool openings 24. The flushing solution together with blood and/or excised tissue and other debris produced during the removal of a blockage is drawn into a suitable receptacle (not shown).

The motor 19 turns the inner hollow tubular member to rotate the cutter head or cutting tool at relatively high speed (up to 3000 rpm). The catheter is advanced and adjusted laterally using modest pressure between the tool and the stenotic lesion and precisely aimed and controlled by means of the guidewire 17. Once the atheroma has been completely excised about the periphery of the vessel, substantially full blood flow through the vessel is restored. It will be appreciated that the position and attitude of the cutter head within the vessel can be continually adjusted during the excising procedure utilizing the guidewire to improve control and precision assuring a more complete removal of the blockage.

The cutting head openings 24 are preferably placed close to the nose so that tissue located directly to the side of the tool including vessel walls or vessel wall linings are not damaged. This normally would result in a less than complete removal of the stenotic lesion from the vessel, although the vessel may be substantially reopened. The provision of the guidewire 17, however, allows the operator to carefully manipulate the cutting head of the catheter during excision, to achieve a more complete clearing of the blockage.

This invention has been described herein in considerable detail in order to comply with the patent statutes and to provide those skilled in the art with the information needed to apply the novel principles and to construct and use such specialized components as are required. However, it is to be understood that the invention can be carried out by specifically different equipment and devices and that various modifications, both as to equipment details and operating procedures, can be accomplished without departing from the scope of the invention itself.

What is claimed is:

1. A method of excising undesirable deposits from a site of interest in the interior of a blood vessel of interest of a patient comprising the steps of:
   (a) introducing a guidewire into the vascular system of the patient and advancing the distal tip of the guidewire through the vascular system to the vicinity of the site of interest;
   (b) providing a coaxial multi-lumen catheter having inner and outer tubular members including a driven rotary cutting tool at the distal end of the inner tubular member and a guidewire port comprising a hollow tubular appendage at the distal end of the outer tubular member;
   (c) locating the hollow tubular appendage just proximal the cutting tool and fixed to and spaced from the outer tubular member to a point beyond the radius of the cutting tool to prevent interference between the guidewire and the cutting tool;
   (d) inserting said catheter into the vascular system and advancing the hollow tubular appendage thereof over the guidewire navigating the vascular system to the vicinity of the site of interest;
   (e) positioning the cutting tool at the site of interest;
   (f) operating the cutting tool to excise the undesirable deposits while independently controlling the position of the cutting tool by means of the guidewire;
   (g) while operating the cutting tool, rotating the catheter including the cutting tool about the guidewire and adjusting the angular position thereof relative to the blood vessel of interest to effect cutting as necessary throughout an inner surface of the vessel of interest;
   (h) simultaneously perfusing a flushing liquid to cleanse the site of interest and aspirating the flushing liquid along with cutting debris and other material from the site; and
   (i) removing the catheter after excision is completed.

2. The method of claim 1 wherein the flushing liquid is a saline solution.

3. A surgical device for excising deposits from the interior of a blood vessel comprising:
   (a) an outer flexible hollow vascular catheter tube having a proximal and a distal end with at least one radial fluid passage opening formed at or near the distal end thereof;
   (b) an inner flexible hollow catheter tube having a proximal and a distal end coaxially disposed within the outer catheter tube member and further being journaled in the distal end of the outer catheter tube, the distal end of the inner tube extending beyond that of the outer tube;
   (c) a substantially hollow cylindrically symmetric cutting tool fixed to the distal end of the inner catheter tube comprising a generally dome-shaped distal nose portion forming the distal end thereof and containing a plurality of radially disposed cutter openings in communication with a hollow interior and disposed such that an edge thereof excises tissue upon rotation of the cutting tool, the excised tissue being generally directed into the hollow interior of the tool, the hollow interior further being in communication with the hollow interior of the inner tube;
   (d) drive means connected to the proximal end of the inner tube for rotating the inner tube and the cutting tool to excise tissue deposits;
   (e) a guidewire port for receiving a guidewire comprising a hollow, tubular appendage located near the distal end of the outer catheter tube just proximal the cutting tool fixed to and spaced radially from the outer tube to a point beyond the radius of the cutting tool such that a guidewire having its distal end extending through the guidewire port is operable to independently control the disposition of the cutting tool relative to its position and attitude throughout the circumference of the vessel of interest, the position of the guidewire port to prevent interference between the guidewire and the cutting tool.

4. The apparatus of claim 3 further comprising perfusion means for introducing a flushing liquid into the lumen of the outer tube outside of the inner tube and perfusing the liquid through the at least one radial fluid passage near the distal end thereof and aspiration means for aspirating liquids through the cutting tool openings via the lumen of the inner tube.

5. The apparatus of claim 4 wherein the distal portion of the outer catheter tube includes a necked-down segment of reduced diameter to prevent clogging thereof during passage of the catheter through the vascular system and has a plurality of symmetrically placed radial fluid passage holes at the location of the segment of reduced diameter.

6. The apparatus of claim 3 wherein the distal portion of the outer catheter tube includes a necked-down segment of reduced diameter to prevent clogging thereof during passage of the catheter through the vascular system and has a plurality of symmetrically placed radial fluid passage holes at the location of the segment of reduced diameter.

7. A surgical device for excising deposits from the interior of a blood vessel comprising:
   (a) an outer flexible hollow vascular catheter tube having a proximal end and a distal end, the distal end portion including a segment of reduced diameter from that of the remaining length of the outer tube and at least one radial fluid port opening formed in the area of reduced diameter;
   (b) a flexible hollow inner catheter tube coaxially disposed within the outer tube and having a proximal end and a distal end and an outer surface, said outer surface being journaled in the necked-down portion of the outer tube, the distal end of the inner tube extending beyond the outer tube;

(c) a generally cylindrical cutting tool having a generally dome-shaped distal nose portion and a hollow interior fixed to the distal end of the inner tube, the nose portion further comprising one or more radially disposed openings extending along and rearward from a point near the center thereof, each said opening being in communication with said hollow interior and disposed such that a cutting edge thereof contacts and excises tissue upon rotation of the cutting tool, excised tissue being directed into said hollow interior, said hollow interior further being connected to the interior of said inner catheter tube;

(d) drive means connected to the proximal end of the inner catheter tube for rotating the inner catheter tube member thereby rotating the cutting tool to excise deposits;

(e) a guidewire port for receiving a guidewire operable to independently control the disposition, including the attitude, of the cutting tool with respect to vascular deposits comprising a hollow tubular appendage located near the distal end of the outer catheter tube just proximal the cutting tool and fixed in parallel spaced relation to the outer tube at a point beyond the radius of the cutting tool to prevent interference between a guidewire having its distal end extending through the guidewire port and the cutting tool.

8. The apparatus of claim 7 further comprising:

infusion means associated with the drive means for introducing a flushing liquid between the inner and outer catheter tubes, the flushing liquid exiting the lumen of the outer catheter tube through the at least one radial fluid passing opening; and aspiration means associated with the drive means for aspirating liquids and excised debris through the plurality of openings in the distal end portion of the cutting tool, via the lumen of the inner catheter tube and out the proximal end of the inner catheter tube.

* * * * *